(12) United States Patent
Bae et al.

(10) Patent No.: US 12,014,493 B2
(45) Date of Patent: Jun. 18, 2024

(54) METHOD AND APPARATUS FOR BONE AGE ASSESSMENT

(71) Applicant: VUNO Inc., Seoul (KR)

(72) Inventors: Byeonguk Bae, Incheon (KR); Kyuhwan Jung, Seoul (KR)

(73) Assignee: VUNO Inc., Seoul (KR)

( * ) Notice: Subject to any disclaimer, the term of this patent is extended or adjusted under 35 U.S.C. 154(b) by 269 days.

(21) Appl. No.: 17/360,897

(22) Filed: Jun. 28, 2021

(65) Prior Publication Data
US 2021/0407081 A1   Dec. 30, 2021

(30) Foreign Application Priority Data

Jun. 29, 2020  (KR) .................. 10-2020-0079491
Aug. 19, 2020  (KR) .................. 10-2020-0103745

(51) Int. Cl.
*G06T 7/00*    (2017.01)
*G06N 3/045*   (2023.01)
*G06N 3/08*    (2023.01)

(52) U.S. Cl.
CPC .......... *G06T 7/0012* (2013.01); *G06N 3/045* (2023.01); *G06N 3/08* (2013.01); *G06T 2207/20081* (2013.01); *G06T 2207/20084* (2013.01); *G06T 2207/30008* (2013.01)

(58) Field of Classification Search
None
See application file for complete search history.

(56) References Cited

U.S. PATENT DOCUMENTS

| | | | |
|---|---|---|---|
| 9,153,021 B2 | 10/2015 | Wilson | |
| 10,242,293 B2 | 3/2019 | Shim et al. | |
| 2020/0020097 A1* | 1/2020 | Do | G06F 18/2413 |
| 2020/0372633 A1* | 11/2020 | Lee | G06N 3/045 |

FOREIGN PATENT DOCUMENTS

| | | | | |
|---|---|---|---|---|
| CN | 110310292 A | * | 10/2019 | ........... G06N 3/0454 |
| JP | 5426170 B2 | | 2/2014 | |
| KR | 10-1846370 B1 | | 4/2018 | |
| KR | 10-1961215 B1 | | 3/2019 | |

(Continued)

OTHER PUBLICATIONS

Aziz et al., "Fast and Robust Generation of Feature Maps for Region-Based Visual Attention," May 2008, in IEEE Transactions on Image Processing, vol. 17, No. 5, pp. 633-644 (Year: 2008).*

(Continued)

*Primary Examiner* — Emily C Terrell
*Assistant Examiner* — Julia Z. Yao
(74) *Attorney, Agent, or Firm* — Seed IP Law Group LLP

(57) ABSTRACT

According to an embodiment of the present disclosure, a method of assessing bone age by using a neural network performed by a computing device is disclosed. The method includes receiving an analysis image which is a target of bone age assessment; and assessing bone age of the target by inputting the analysis image into a bone age analysis model comprising one or more neural networks. The bone age analysis model, which is trained by supervised learning based on an attention guide label, includes at least one attention module for intensively analyzing a main region of the analysis image.

10 Claims, 8 Drawing Sheets

(56) References Cited

FOREIGN PATENT DOCUMENTS

KR    10-2019-0059364 A    5/2019

OTHER PUBLICATIONS

Kim et al., "Spatially Attentive Output Layer for Image Classification," 2020, 2020 IEEE/CVF Conference on Computer Vision and Pattern Recognition (CVPR), pp. 9530-9539 (Year: 2020).*

Woo et al., "CBAM: Convolutional Block Attention Module," 2018, Cham Springer, European Conference on Computer Vision (ECCV) 2018, pp. 3-19 (Year: 2018).*

H. Lee et al., "Fully Automated Deep Learning System for Bone Age Assessment," 2017, Journal of digital imaging vol. 30,4 (2017): 427-441 (Year: 2017).*

W. Tang et al., "Automatic Radiographic Bone Age Assessment Using Deep Joint Learning with Attention Modules," Jul. 1-10, 2020, IOS Press, vol. 12 of Advances in Transdisciplinary Engineering, pp. 221-230 (Year: 2020).*

Escobar et al., "Hand Pose Estimation for Pediatric Bone Age Assessment," 2019, Medical Image Computing and Computer Assisted Intervention (MICCAI) 2019, Springer International Publishing, pp. 531-539 (Year: 2019).*

Payer et al., "Integrating spatial configuration into heatmap regression based CNNs for landmark localization," 2019, Medical Image Analysis, vol. 54, pp. 207-219, https://doi.org/10.1016/j.media.2019.03.007 (Year: 2019).*

Escobar et al., "Hand Pose Estimation for Pediatric Bone Age Assessment," Medical Image Computing and Computer Assisted Intervention—MICCAI 2019, MICCAI 2019, Lecture Notes in Computer Science( ), vol. 11769, Springer, Cham. https://doi.org/10.1007/978-3-030-32226-7_59 (Year: 2019).*

Wang et al., "Improve bone age assessment by learning from anatomical local regions," May 2020, Medical Image Computing and Computer Assisted Intervention—MICCAI 2020, Lecture Notes in Computer Science( ), Springer, Cham, vol. 12266. https://doi.org/10.1007/978-3-030-59725-2_61 (Year: 2020).*

Pan et al., "Fully Automated Bone Age Assessment on Large-Scale Hand X-Ray Dataset," Int J Biomed Imaging, Mar. 3, 2020;2020:8460493. doi: 10.1155/2020/8460493. (Year: 2020).*

Chu et al., "Bone Age Assessment Based on Two-Stage Deep Neural Networks," 2018 Digital Image Computing: Techniques and Applications (DICTA), Canberra, ACT, Australia, 2018, pp. 1-6, doi: 10.1109/DICTA.2018.8615764. (Year: 2018).*

Chen et al., "ARU-NET: Research and Application for Wrist Reference Bone Segmentation," in IEEE Access, vol. 7, pp. 166930-166938, 2019, doi: 10.1109/ACCESS.2019.2952608. (Year: 2019).*

Liu et al., "Bone Age Assessment Based on Rank—Monotonicity Enhanced Ranking CNN," in IEEE Access, vol. 7, pp. 120976-120983, 2019, doi: 10.1109/ACCESS.2019.2937341. (Year: 2019).*

Zhao et al., "Deeply Supervised Active Learning for Finger Bones Segmentation," May 2020, in IEEE, 2020 42nd Annual International Conference of the IEEE Engineering in Medicine & Biology Society (EMBC). doi: 10.1109/embc44109.2020.9176662 (Year: 2020).*

Litjens et al., "A Survey on Deep Learning in Medical Image Analysis," 2017, Elsevier BV, Medical Image Analysis, vol. 42, pp. 60-88. doi: 10.1016/j.media.2017.07.005 (Year: 2017).*

Iglovikov et al., "Paediatric Bone Age Assessment Using Deep Convolutional Neural Networks," Deep Learning in Medical Image Analysis and Multimodal Learning for Clinical Decision Support (DLMIA ML-CDS) 2018, Lecture Notes in Computer Science( ), vol. 11045, Springer, Cham (Year: 2018).*

Yang et al., "Constrained R-Cnn: A General Image Manipulation Detection Model," 2020 IEEE International Conference on Multimedia and Expo (ICME), London, UK, 2020, pp. 1-6, doi: 10.1109/ICME46284.2020.9102825. (Year: 2020).*

Li, et al., "Tell Me Where to Look: Guided Attention Inference Network," IEEE Transactions on Pattern Analysis and Machine Intelligence, 2019, vol. 42 (12), pp. 9215-9223.

Son, et al., "TW3-Based Fully Automated Bone Age Assessment System Using Deep Neural Networks," IEEE Xplore, 2019 vol. 7, pp. 33346-33358.

Woo, et al., "CBAM: Convolution Block Attention Module," The European Conference on Computer Vision (ECCV), 2018, pp. 1-17.

Chen et al., "SCA-CNN: Spatial and Channel-Wise Attention in Convolutional Networks for Image Captioning," *2017 IEEE Conference on Computer Vision and Pattern Recognition (CVPR)*, Institute for Electrical and Electronics Engineers, Honolulu, HI, Jul. 21-26, 2017, pp. 6298-6306.

Kim et al., "Spatially Attentive Output Layer for Image Classification," *2020 IEEE/CVF Conference on Computer Vision and Pattern Recognition (CVPR)*, Institute for Electrical and Electronics Engineers/Computer Vision Foundation, Seattle, WA, Jun. 13-19, 2020, pp. 9533-9542.

Lee et al., "Fully Automated Deep Learning System for Bone Age Assessment," *J Digit Imaging* 30:427-441, Mar. 8, 2017, 15 pages.

Ren et al., "Regression Convolutional Neural Network for Automated Pediatric Bone Age Assessment From Hand Radiograph," *IEEE Journal of Biomedical and Health Informatics* 23(5):2030-2038, Sep. 2019.

* cited by examiner

METHOD AND APPARATUS FOR BONE AGE ASSESSMENT

CROSS-REFERENCE TO RELATED APPLICATIONS

This application claims priority to and the benefit of Korean Patent Application No. 10-2020-0079491 filed in the Korean Intellectual Property Office on Jun. 29, 2020, and Korean Patent Application No. 10-2020-0103745 filed in the Korean Intellectual Property Office on Aug. 19, 2020 the entire contents of which are incorporated herein by reference.

BACKGROUND

Technical Field

The present disclosure relates to a method of assessing bone age, and more particularly, to a method of assessing bone age by using a neural network.

Description of the Related Art

In the art, Greulich-Pyle method and the Tanner-Whitehouse 3 method are used as the method for assessing the degree of bone development (bone age) from a bone image. The Greulich-Pyle method and the Tanner-Whitehouse 3 are used as ground truth for labeling in the image analysis technology using an artificial neural network.

When a user who trains the artificial neural network knows the ground truth for an input, the user selects a supervised learning method. However, even though the user knows the ground truth, the artificial neural network that generally performs end-to-end learning cannot perform more detailed supervised learning. Accordingly, there has been a general demand in the art as well as in the artificial intelligence-related field that learning proceeds more intensively in a specific area when the user knows ground truth for an input.

The prior paper, "S. J. Son et al., 'TW3-Based Fully Automated Bone Age Assessment System Using Deep Neural Networks,' in IEEE Access, vol. 7, pp. 33346-33358, 2019, doi: 10.1109/ACCESS.2019.2903131," discloses the artificial neural network learning the bone age assessment method in the TW3 method.

BRIEF SUMMARY

The present disclosure is conceived at least partially in response to the background art, and has been made in an effort to provide a method of assessing bone age by using a neural network. Particularly, one or more embodiments of the present disclosure provide a method of training the neural network with supervised learning.

In order to solve the foregoing technical problems as well as other problems in the related art, there is disclosed a method for bone age assessment using neural network performed by a computing device. The method comprises: receiving an analysis image which is a target of bone age assessment; and assessing bone age of the target by inputting the analysis image into a bone age analysis model comprising one or more neural networks, wherein the bone age analysis model, which is trained by supervised learning based on an attention guide label, comprises at least one attention module for intensively analyzing a main region of the analysis image.

Alternatively, the attention guide label may be generated based on a detection result obtained as a result of inputting a training image to a main region detection model comprising at least one neural network, and the detection result may comprise location information on at least one main region comprised in the training image.

Alternatively, when the main region is in a form of a bounding box, the detection result may comprise coordinates of a center point of at least one main region comprised in the training image, a width of the at least one main region comprised in the training image, and a height of the at least one main region comprised in the training image.

Alternatively, the attention guide label may comprise an importance of at least one pixel comprised in a training image, and the pixel may be obtained as a result of substituting a distance between coordinates of the pixel and coordinates of a center point of one or more main regions comprised in the training image to an equation based on a Gaussian distribution.

Alternatively, the bone age analysis model may be trained by supervised learning based on at least one training image and the attention guide label which corresponds to each of the training image and comprises at least one main region, and wherein the supervised learning may be performed based on a comparison result of a spatial attention map generated regarding the training image using the bone age analysis model and the attention guide label corresponding to the training image.

Alternatively, the supervised learning may be performed based on a result calculated by substituting the spatial attention map and the attention guide label into a binary cross-entropy loss function.

Alternatively, when the bone age analysis model comprises at least two attention modules, the supervised learning on the bone age analysis model may be performed based on a result of multiplying a result of a loss function calculated in each attention module by the weight according to the predetermined attention module and then summing.

Alternatively, the attention module may comprise a channel attention neural network model for generating a channel attention map regarding a feature map input to the attention module and a spatial attention neural network model for generating a spatial attention map regarding a modified feature map, and the modified feature map may be a feature map generated by multiplying the feature map input to the attention module by the channel attention map for each element.

In order to solve the foregoing technical problems in the related art, there is disclosed a method for bone age assessment using neural network performed by a computing device. The method may comprise: receiving an analysis image which is a target of bone age assessment; assessing bone age of the target by inputting the analysis image into a bone age analysis model comprising at least one neural network; and providing a user interface screen comprising a heat map generated based on a spatial attention map for the analysis image, wherein the bone age analysis model, which is trained by supervised learning based on an attention guide label, comprises at least one attention module for intensively analyzing a main region of the analysis image.

In order to solve the foregoing technical problems in the related art, there is disclosed a method for bone age assessment using neural network performed by a computing device. The method comprises: receiving an analysis image which is a target of bone age assessment; assessing bone age of the target by inputting the analysis image into a bone age analysis model comprising at least one neural network; and providing a user interface screen comprising a heat map generated based on a spatial attention map for the analysis image, and the attention module comprised in the bone age analysis model may comprise: a channel attention neural network model for generating a channel attention map regarding a feature map input to the attention module; and a spatial attention neural network model for generating a spatial attention map regarding a modified feature map, and the modified feature map may be a feature map in which the channel attention map is multiplied for each element by a feature map input to the attention module.

In order to solve the foregoing technical problems in the related art, there is disclosed a computer program stored in a computer readable storage medium. When the computer program is executed in one or more processors, the program causes one or more processors to perform following operations for assessing bone age by using a neural network, the operations including inputting an analysis image which is a target of bone age assessment to a bone age analysis model including one or more neural networks and assessing bone age, wherein the bone age analysis model comprises one or more attention modules for intensively analyzing a main region of the analysis image, and the bone age analysis model is trained with supervised learning based on an attention guide label.

In order to solve the foregoing technical problems in the related art, there is disclosed a device for bone age assessment. The device comprises: one or more processors; a memory for storing a bone age analysis model comprising one or more neural networks; and a network unit for receiving an analysis image which is a target of bone age assessment, in which the one or more processors is configured to assess bone age of the target by inputting the analysis image into a bone age analysis model comprising one or more neural networks, and the bone age analysis model, which is trained by supervised learning based on an attention guide label, comprises at least one attention module for intensively analyzing a main region of the analysis image.

The present disclosure may provide the method of assessing bone age by using a neural network.

DETAILED DESCRIPTION

Figure 1:
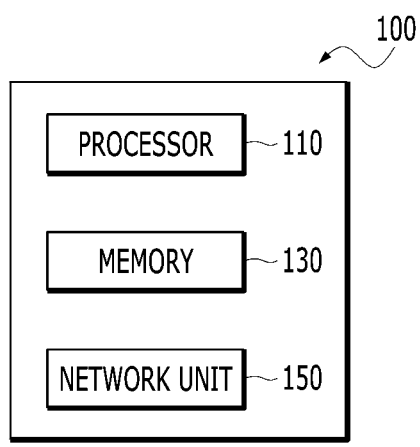
FIG. 1 is a block diagram of a computing device for assessing bone age according to an embodiment of the present disclosure.

Various embodiments are described with reference to the drawings. In the present specification, various descriptions are presented for understanding the present disclosure. However, it is obvious that the embodiments may be carried out even without a particular description.

Terms, "component," "module," "system," and the like used in the present specification indicate a computer-related entity, hardware, firmware, software, a combination of software and hardware, or execution of software. For example, a component may be a procedure executed in a processor, a processor, an object, an execution thread, a program, and/or a computer, but is not limited thereto. For example, both an application executed in a computing device and a computing device may be components. One or more components may reside within a processor and/or an execution thread. One component may be localized within one computer. One component may be distributed between two or more computers. Further, the components may be executed by various computer readable media having various data structures stored therein. For example, components may communicate through local and/or remote processing according to a signal (for example, data transmitted to another system through a network, such as the Internet, through data and/or a signal from one component interacting with another component in a local system and a distributed system) having one or more data packets.

A term "or" intends to mean comprehensive "or" not exclusive "or." That is, unless otherwise specified or when it is unclear in context, "X uses A or B" intends to mean one of the natural comprehensive substitutions. That is, when X uses A, X uses B, or X uses both A and B, "X uses A or B" may be applied to any one among the cases. Further, a term "and/or" used in the present specification shall be understood to designate and include all of the possible combinations of one or more items among the listed relevant items.

It should be understood that a term "include" and/or "including" means that a corresponding characteristic and/or a constituent element exists. Further, a term "include" and/or "including" means that a corresponding characteristic and/or a constituent element exists, but it shall be understood that the existence or an addition of one or more other characteristics, constituent elements, and/or a group thereof is not excluded. Further, unless otherwise specified or when it is unclear in context that a single form is indicated in context, the singular shall be construed to generally mean "one or more" in the present specification and the claims.

The term "at least one of A and B" should be interpreted to mean "the case including only A," "the case including only B," and "the case where A and B are combined."

Those skilled in the art shall recognize that the various illustrative logical blocks, configurations, modules, circuits, means, logic, and algorithm operations described in relation to the embodiments additionally disclosed herein may be implemented by electronic hardware, computer software, or in a combination of electronic hardware and computer software. In order to clearly exemplify interchangeability of hardware and software, the various illustrative components, blocks, configurations, means, logic, modules, circuits, and operations have been generally described above in the functional aspects thereof. Whether the functionality is implemented as hardware or software depends on a specific application or design restraints given to the general system. Those skilled in the art may implement the functionality described by various methods for each of the specific applications. However, it shall not be construed that the determinations of the implementation deviate from the range of the contents of the present disclosure.

The description about the presented embodiments is provided so as for those skilled in the art to use or carry out the present disclosure. Various modifications of the embodiments will be apparent to those skilled in the art. General principles defined herein may be applied to other embodiments without departing from the scope of the present disclosure. Therefore, the present disclosure is not limited to the embodiments presented herein. The present disclosure shall be interpreted within the broadest meaning range consistent to the principles and new characteristics presented herein.

In the present disclosure, a network function, an artificial neural network, and a neural network may be interchangeably used.

The term "image" or "image data" used throughout the detailed description and the claims of the present disclosure refer to multidimensional data composed of discrete image elements (for example, pixels in a 2-dimensional image), and in other words, is the term referring to a target visible to the eye (displayed on a video screen) or a digital representation of the target (for example, a file corresponding to a pixel output of a CT or MRI detector).

For example, in the present disclosure, "image" or "picture" may be a medical image of a subject collected by Computed Tomography (CT), Magnetic Resonance Imaging (MRI), fundus image, ultrasonic rays, or other predetermined (or selected) medical imaging systems publicly known in the art of the present disclosure. The image is not necessarily provided in a medical context, but may also be provided in a non-medical context, such as X-ray imaging for security screening.

Throughout the detailed description and the claims of the present disclosure, the "Digital Imaging and Communications in Medicine (DICOM)" standard is a term collectively referring to various standards used in digital imaging expression and communication in medical devices, and the DICOM standard is published by the allied committee formed by the American College of Radiology (ACR) and American National Electrical Manufacturers Associations (NEMA).

Throughout the detailed description and the claims of the present disclosure, a "Picture Archiving and Communication System (PACS)" is a term that refers to a system that stores, processes, and transmits images in accordance with the DICOM standard, and medical images obtained by using digital medical imaging equipment, such as X-ray, CT, and MRI, may be stored in the DICOM format and transmitted to terminals inside and outside a hospital through a network, and a reading result and a medical record may be added to the medical image.

FIG. 1 is a block diagram of a computing device for assessing bone age according to an embodiment of the present disclosure.

The configuration of a computing device 100 illustrated in FIG. 1 is merely a simplified example. In the embodiment of the present disclosure, the computing device 100 may include other configurations for performing a computing environment of the computing device 100, and only some of the disclosed configurations may also configure the computing device 100.

The computing device 100 may include a processor 110, a memory 130, and a network unit 150.

The processor 110 may be formed of one or more cores, and may include a processor, such as a central processing unit (CPU), a general purpose graphics processing unit (GPGPU), and a tensor processing unit (TPU) of the computing device, for performing a data analysis and deep learning. The processor 110 may read a computer program stored in the memory 130 and process data for machine learning according to an embodiment of the present disclosure. According to the embodiment of the present disclosure, the processor 110 may perform calculation for training a neural network. The processor 110 may perform a calculation, such as processing of input data for training in Deep Learning (DN), extraction of a feature from input data, an error calculation, and updating of a weight of the neural network by using backpropagation, for training the neural network. At least one of the CPU, GPGPU, and TPU of the processor 110 may process training of a network function. For example, the CPU and the GPGPU may process training of the network function and data classification by using a network function together. Further, in the embodiment of the present disclosure, the training of the network function and the data classification by using a network function may be processed by using the processors of the plurality of computing devices together. Further, the computer program executed in the computing device according to the embodiment of the present disclosure may be a CPU, GPGPU, or TPU executable program.

According to the embodiment of the present disclosure, the memory 130 may store a predetermined (or selected) type of information generated or determined by the processor 110 and a predetermined (or selected) type of information received by a network unit 150.

According to the embodiment of the present disclosure, the memory 130 may include at least one type of storage medium among a flash memory type, a hard disk type, a multimedia card micro type, a card type of memory (for example, an SD or XD memory), a Random Access Memory (RAM), a Static Random Access Memory (SRAM), a Read-Only Memory (ROM), an Electrically Erasable Programmable Read-Only Memory (EEPROM), a Programmable Read-Only Memory (PROM), a magnetic memory, a magnetic disk, and an optical disk. The computing device 100 may also be operated in relation to web storage performing a storage function of the memory 130 on the Internet. The description of the foregoing memory is merely illustrative, and the present disclosure is not limited thereto.

The network unit 150 according to several embodiments of the present disclosure may use various wired communication systems, such as a Public Switched Telephone Network (PSTN), an x Digital Subscriber Line (xDSL), a Rate Adaptive DSL (RADSL), a Multi Rate DSL (MDSL), a Very High Speed DSL (VDSL), a Universal Asymmetric DSL (UADSL), a High Bit Rate DSL (HDSL), and a local area network (LAN).

The network unit 150 presented in the present specification may use various wireless communication systems, such as Code Division Multi Access (CDMA), Time Division Multi Access (TDMA), Frequency Division Multi Access (FDMA), Orthogonal Frequency Division Multi Access (OFDMA), Single Carrier-FDMA (SC-FDMA), and other systems.

The network unit 150 in the present disclosure may be configured regardless of its communication mode, such as a wired mode and a wireless mode, and may be configured of various communication networks, such as a Personal Area Network (PAN) and a Wide Area Network (WAN). Further, the network may be the publicly known World Wide Web (WWW), and may also use a wireless transmission technology used in PAN, such as Infrared Data Association (IrDA) or Bluetooth.

The technologies described in the present specification may be used in other networks, as well as the foregoing networks.

A method of bone age assessment using a neural network performed by a computing device of the present disclosure may include: receiving an analysis image which is a target of bone age assessment; and assessing bone age by inputting the analysis image to a bone age analysis model including one or more neural networks. Further, the bone age analysis model includes at least one attention module for intensively analyzing a main region of the analysis image and is trained by supervised learning based on an attention guide label.

In the embodiment of the present disclosure, the network unit 150 included in the computing device 100 may receive an analysis image which is a target of bone age assessment. The bone age assessment means measuring or predicting bone maturity from a bone-related medical image. The analysis image may be a bone-related image that requires reading. In the present specification, the "image" may be used as a concept that includes all kinds of medical images that can be input to a bone age assessment model, including an analysis image or training image. Accordingly, in the present disclosure, the analysis image or the training image which is a target of the bone age assessment may include, for example, at least one of a bone-related X-ray image, a CT image, and an MM image provided to determine bone age. Further, the analysis image or the training image may include any bone-related image that may be a target of bone age assessment, such as a hand bone, an elbow bone, and a knee bone, without limitation. The training image is the image used for training of the bone age assessment model, and may be distinguished from the analysis image, which is an image input in an inference operation of the bone age assessment model.

In the embodiment of the present disclosure, the processor 110 included in the computing device 100 may assess bone age by inputting the analysis image to a bone age analysis model including one or more neural networks.

Figure 2:
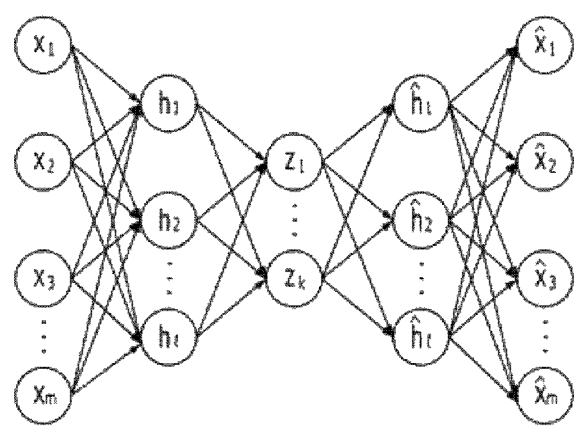
FIG. 2 is a schematic diagram illustrating a network function according to the embodiment of the present disclosure.

FIG. 2 is a schematic diagram illustrating a network function according to the embodiment of the present disclosure.

Throughout the present specification, a calculation model, a nerve network, the network function, and the neural network may be used with the same meaning. The neural network may be formed of a set of interconnected calculation units which are generally referred to as "nodes". The "nodes" may also be called "neurons". The neural network consists of one or more nodes. The nodes (or neurons) configuring the neural network may be interconnected by one or more links.

In the neural network, one or more nodes connected through the links may relatively form a relationship of an input node and an output node. The concept of the input node is relative to the concept of the output node, and a predetermined (or selected) node having an output node relationship with respect to one node may have an input node relationship in a relationship with another node, and a reverse relationship is also available. As described above, the relationship between the input node and the output node may be generated based on the link. One or more output nodes may be connected to one input node through a link, and a reverse case may also be valid.

In the relationship between an input node and an output node connected through one link, a value of the output node data may be determined based on data input to the input node. Herein, a link connecting the input node and the output node may have a weight. The weight is variable, and in order for the neural network to perform a desired (or selected) function, the weight may be varied by a user or an algorithm. For example, when one or more input nodes are connected to one output node by links, respectively, a value of the output node may be determined based on values input to the input nodes connected to the output node and weights set in the link corresponding to each of the input nodes.

As described above, in the neural network, one or more nodes are connected with each other through one or more links to form a relationship of an input node and an output node in the neural network. A characteristic of the neural network may be determined according to the number of nodes and links in the neural network, a correlation between the nodes and the links, and a value of the weight assigned to each of the links. For example, when there are two neural networks in which the numbers of nodes and links are the same and each of the links has a different weight, the two neural networks may be recognized to be different from each other.

The neural network may consist of a set of one or more nodes. A subset of the nodes forming the neural network may form a layer. Some of the nodes configuring the neural network may form one layer based on distances from an initial input node. For example, a set of nodes having a distance of n from an initial input node may form n layers. The distance from the initial input node may be defined by the minimum number of links, which need to be passed from the initial input node to a corresponding node. However, the definition of the layer is arbitrary for the description, and a degree of the layer in the neural network may be defined by a different method from the foregoing method. For example, the layers of the nodes may be defined by a distance from a final output node.

The initial input node may mean one or more nodes to which data is directly input without passing through a link in a relationship with other nodes among the nodes in the neural network. Otherwise, the initial input node may mean nodes which do not have other input nodes connected through the links in a relationship between the nodes based on the link in the neural network. Similarly, the final output node may mean one or more nodes that do not have an output node in a relationship with other nodes among the nodes in the neural network. Further, the hidden node may mean nodes configuring the neural network, not the initial input node and the final output node.

In the neural network according to the embodiment of the present disclosure, the number of nodes of the input layer may be the same as the number of nodes of the output layer, and the neural network may be in the form that the number of nodes decreases and then increases again from the input layer to the hidden layer. Further, in the neural network according to another embodiment of the present disclosure, the number of nodes of the input layer may be smaller than the number of nodes of the output layer, and the neural network may be in the form that the number of nodes decreases from the input layer to the hidden layer. Further, in the neural network according to another embodiment of the present disclosure, the number of nodes of the input layer may be larger than the number of nodes of the output layer, and the neural network may be in the form that the number of nodes increases from the input layer to the hidden layer. The neural network according to another embodiment of the present disclosure may be the neural network in the form in which the foregoing neural networks are combined.

A deep neural network (DNN) may mean the neural network including a plurality of hidden layers, in addition to an input layer and an output layer. When the DNN is used, it is possible to recognize a latent structure of data. That is, it is possible to recognize the latent structures of pictures, texts, videos, voices, and music (for example, an object included in the picture, the contents and the emotion of the text, and the contents and the emotion of the voice). The DNN may include a convolutional neural network (CNN), a recurrent neural network (RNN), an auto encoder, Generative Adversarial Networks (GAN), a restricted Boltzmann machine (RBM), a deep belief network (DBN), a Q network, a U network, Siamese network, and the like. The foregoing description of the deep neural network is merely illustrative, and the present disclosure is not limited thereto.

In the embodiment of the present disclosure, the network function may include an auto encoder. The auto encoder may be one type of artificial neural network for outputting output data similar to input data. The auto encoder may include at least one hidden layer, and the odd-numbered hidden layers may be disposed between the input/output layers. The number of nodes of each layer may decrease from the number of nodes of the input layer to an intermediate layer called a bottleneck layer (encoding), and then be expanded symmetrically with the decrease from the bottleneck layer to the output layer (symmetric with the input layer). The auto encoder may perform a nonlinear dimension reduction. The number of input layers and the number of output layers may correspond to the dimensions after preprocessing of the input data. In the auto encoder structure, the number of nodes of the hidden layer included in the encoder decreases as a distance from the input layer increases. When the number of nodes of the bottleneck layer (the layer having the smallest number of nodes located between the encoder and the decoder) is too small, the sufficient amount of information may not be transmitted, so that the number of nodes of the bottleneck layer may be maintained in a specific number or more (for example, a half or more of the number of nodes of the input layer and the like).

The neural network may be trained by at least one scheme of supervised learning, unsupervised learning, semi-supervised learning, and reinforcement learning. The training of the neural network may be a process of applying knowledge for performing, by the neural network, a specific operation, to the neural network.

The neural network may be trained in a direction of reducing or minimizing an error of an output. In the training of the neural network, training data is repeatedly input to the neural network and an error of an output of the neural network for the training data and a target is calculated, and the error of the neural network is back-propagated in a direction from an output layer to an input layer of the neural network in order to decrease the error, and a weight of each node of the neural network is updated. In the case of the supervised learning, training data labelled with a correct answer (that is, labelled training data) is used, in each training data, and in the case of the unsupervised learning, a correct answer may not be labelled to each training data. That is, for example, the training data in the supervised learning for data classification may be data, in which category is labelled to each of the training data. The labelled training data is input to the neural network and the output (category) of the neural network is compared with the label of the training data to calculate an error. For another example, in the case of the unsupervised learning related to the data classification, training data that is the input is compared with an output of the neural network, so that an error may be calculated. The calculated error is back-propagated in a reverse direction (that is, the direction from the output layer to the input layer) in the neural network, and a connection weight of each of the nodes of the layers of the neural network may be updated according to the backpropagation. A variation rate of the updated connection weight of each node may be determined according to a learning rate. The calculation of the neural network for the input data and the backpropagation of the error may configure a learning epoch. The learning rate is differently applicable according to the number of times of repetition of the learning epoch of the neural network. For example, at the initial stage of the learning of the neural network, a high learning rate is used to make the neural network rapidly secure performance of a predetermined (or selected) level and improve efficiency, and at the latter stage of the learning, a low learning rate is used to improve accuracy.

In the learning of the neural network, the training data may be generally a subset of actual data (that is, data to be processed by using the learned neural network), and thus an error for the training data is decreased, but there may exist a learning epoch, in which an error for the actual data is increased. Overfitting is a phenomenon, in which the neural network excessively learns training data, so that an error for actual data is increased. For example, a phenomenon, in which the neural network learning a cat while seeing a yellow cat cannot recognize cats, other than a yellow cat, as cats, is a sort of overfitting. Overfitting may act as a reason of increasing an error of a machine learning algorithm. In order to prevent overfitting, various optimizing methods may be used. In order to prevent overfitting, a method of increasing training data, a regularization method, a dropout method of inactivating a part of nodes of the network during the learning process, a method using a batch normalization layer, and the like may be applied.

Hereinafter, a structure of the bone age analysis model including the one or more neural networks will be described.

In the embodiment of the present disclosure, the bone age analysis model may include at least one attention module for intensively analyzing a main region of the analysis image. The main region is a concept meaning a part of the image to be intensively considered in the process of calculating, by the processor 110, a final output in the image through the bone age analysis model. The image may include a training image used during the training of the bone age analysis model and an analysis image used for inference through the bone age analysis model.

In the embodiment of the present disclosure, the main region may include a partial region related to at least one hand joint to be checked in the Tanner-Whitehouse 3 (TW3) of the bone age assessment method. In another embodiment, the main region may include at least one partial region according to the TW2 method, at least one partial region required to be checked to estimate bone age from the elbow joint image, and the like. The foregoing example for the main region is merely illustrative, and the present disclosure includes, without limitation, the main region which the analysis model needs to intensively reflect for assessing the bone age from the bone-related image. In the embodiment of the present disclosure, the main region may include a coordinate, a width, a height, and the like of a pixel.

In the embodiment of the present disclosure, the attention module included in the bone age analysis model may adjust an internal value of the feature map related to the main region so that at least one block or node which is connected with the attention module and configures a next layer of the bone age analysis model is significantly affected by the internal value of the feature map related to the main region rather than an internal value of the feature map unrelated with the main region. The feature map may include at least one of intermediate output feature maps of several neural network layers included in the bone age analysis model in a computation process for the analysis image or the training image input to the bone age analysis model. The feature map may have a three-dimensional size as a result of the generation of the two-dimensional array as many as the number of channels according to the type of filter. Otherwise, the feature map may also have a predetermined (or selected) N-dimensional size. The internal value of the feature map may mean data included in the multi-dimensional array. The data may be expressed with a real number. The adjustment of the internal value of the feature map related to the main region of the attention module may include a computation of amplifying an absolute value of the internal value of the related feature map through learning of an appropriate weight, a computation of decreasing an absolute value of an internal value of an unrelated feature map.

The attention module in the embodiment of the present disclosure may include a channel attention neural network model for generating a channel attention map for the feature map input to the attention module, and a spatial attention neural network model for generating a spatial attention map for a modified feature map. The corrected feature map may be a feature map in which the channel attention map is multiplied for each element by a feature map input to the attention module. The attention module may exist at a predetermined (or selected) location between other blocks, rather than the attention module included in the bone age analysis model, and at least one attention module may exist. Inside the attention module, the channel attention neural network model and the spatial attention neural network model may maintain, for example, a serial connection structure in which the channel attention neural network precedes and the spatial attention neural network model follows.

The channel attention neural network model in the embodiment of the present disclosure may apply a pooling method to the two-dimensional array corresponding to each channel according to a channel axis of the feature map in the feature map input to the three-dimensional attention module and generate the channel attention map based on the result of the application. The pooling method may include a global max pooling method or a global average pooling method. In particular, the channel attention neural network model may input the feature map to which the pooling method is applied to a first network function including at least one connection weight or bias and generate the channel attention map as a result. Two or more feature maps to which the pooling method is applied may also be generated according to the type of pooling method.

For example, it is assumed that the feature map input to the attention module has a multi-dimensional array having a height of 64, a width of 64, and a size of channel C. For the feature map having the size of 64×64×C, the processor 110 may generate a channel attention intermediate feature map having a size of 1×1×C by applying the pooling method along the channel axis through the channel attention neural network model. The channel attention intermediate feature map may substantially have the one-dimensional array. The channel attention intermediate feature map may include, for example, a first channel attention intermediate feature map to which the global average pooling method is applied and a second channel attention intermediate feature map to which the global max pooling method is applied. The channel attention neural network model may input at least one of the channel attention intermediate feature maps to the first network function, and generate the channel attention map as a result. For example, the first network function may be formed of a multi-layer perceptron including one or more hidden layers. When the first network function is formed of the multi-layer perceptron, in order to decrease the numbers of connection weights and biases and increase a computation speed, the number of nodes of the hidden layer may be less than the size of the channel attention intermediate feature map by a predetermined (or selected) percentage or less. At least one connection weight or bias included in the first network function may be supervised learned by the label for the channel attention map, and may be semi-supervised learned in the training process of the spatial attention neural network model which to be described below. The examples of the size of the array or the type of first network function are merely illustrative, and the present disclosure is not limited thereto.

The spatial attention neural network model in the embodiment of the present disclosure may generate a spatial attention map for the modified feature map. The modified feature map means the feature map generated as a result of applying the channel attention map generated by the channel attention neural network model to the feature map input to the attention model. The modified feature map may be generated as a result of element-wise multiplication of the feature map input to the attention module and the channel attention map. The spatial attention neural network model of the present disclosure generates the spatial attention map for the modified feature map, so that the attention module of the present disclosure may obtain an effect of disposing the channel attention neural network model and the spatial attention neural network model in a predetermined (or selected) order.

In the present disclosure, the element-wise multiplication may include a calculation of multiplying elements at the same position when the sizes of the two multi-dimensional arrays are the same. The element-wise multiplication may include a calculation of multiplying the elements of the same position after making the sizes of the arrays be the same through a broadcasting method when the sizes of the two multi-dimensional arrays are different from each other. The broadcasting method means the method of duplicating one array to have the same size as the other array when the sizes of the two arrays are different from each other. For example, when a first array to be multiplied by each element has a size of 64×64×C and a second array has a size of 1×1×C, two arrays have the same number of channels of size "C", but are "64" times different in height and width, so that an array having the size of 64×64×C may be generated by duplicating the second array and concatenating the second array in the height and width directions, and then the first array and each element may be multiplied. For another example, when a first array to be multiplied by each element has a size of 64×64×C and a second array has a size of 64×64×1, two arrays have the same height and width of size "64", but are "C" times different in the number of channels, so that an array having the size of 64×64×C may be generated by duplicating the second array and concatenating the second array in the channel direction, and then the first array and each element may be multiplied. The example for the multiplication for each element is merely illustrative, and the present disclosure is not limited.

The spatial attention neural network model in the embodiment of the present disclosure may apply the pooling method to the one-dimensional array corresponding to each of the coordinates (h,w) along the height (H) axis or width (W) axis vertical to the channel axis in the three-dimensional modified feature map and generate the spatial attention map based on the application. The coordinates (h,w) refer to coordinates on a two-dimensional plane consisting of a height axis and a width axis other than the channel axis in the three-dimensional feature map. The one-dimensional array corresponding to the coordinates (h,w) means the array including data corresponding to each of the entire channels. The pooling method may include the global max pooling method or the global average pooling method.

For example, it is assumed that the feature map modified according to the application of the channel attention map has a multi-dimensional array having a height of 64, a width of 64, and a size of channel C. In this case, the processor 110 may generate the spatial attention intermediate feature map having the size of 64×64×1 by applying the pooling method to the entire channels corresponding to the coordinates (h,w) along the height (H) axis or width (W) axis of the modified feature map through the spatial attention neural network model. Two or more spatial attention intermediate feature maps may be generated according to the type of pooling method. The spatial attention intermediate feature map may include, for example, a first spatial attention intermediate feature map based on the global average pooling method or a second spatial attention intermediate feature map based on the global max pooling method. The spatial attention neural network model may input the spatial attention intermediate feature map to a second network function and generate a spatial attention map as a result. The second network function may consist of, for example, a Convolution Artificial Neural Network (CNN) including one or more nodes. The CNN of the second network function may be trained through supervised learning, and the learning method will be described below in detail. The spatial attention neural network model may generate the spatial attention map by inputting at least one spatial attention intermediate feature map to the second network function.

Figure 3:
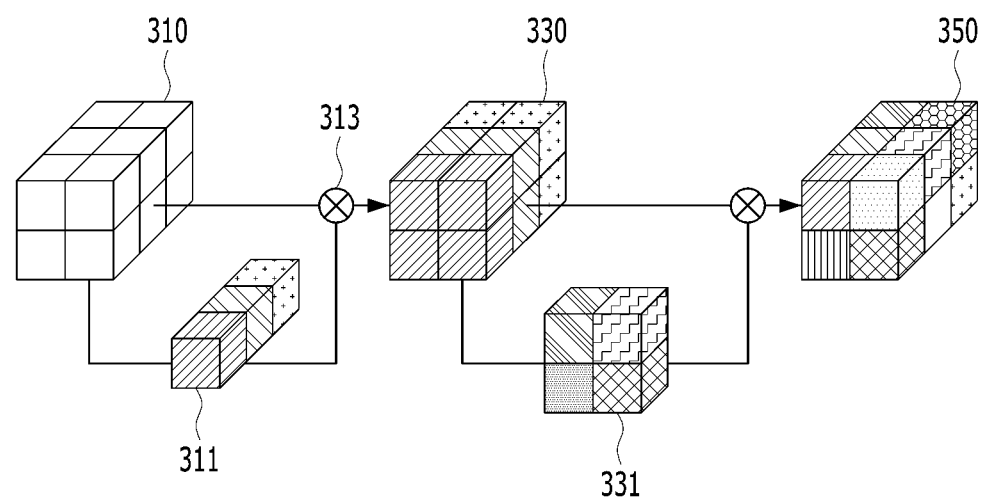
FIG. 3 is a diagram illustrating an example of a structure of an attention module according to the embodiment of the present disclosure.

Hereinafter, the attention module will be additionally described with reference to FIG. 3. FIG. 3 is a diagram illustrating an example of a structure of the attention module according to the embodiment of the present disclosure. The processor 110 in the embodiment of the present disclosure inputs a feature map 310 input to the attention module to the channel attention neural network model and then generates a channel attention map 311. Then, the processor 110 element-wise multiplies 313 the channel attention map 311 and the feature map 310 input to the attention module and generates the modified feature map 330. In this case, the channel attention map 311 has half the height and width of the feature map 310 input to the attention module, so that the processor 110 performs the broadcasting and then performs the element-wise multiplication 313 as described above. The processor 110 inputs the modified feature map 330 to the spatial attention neural network model and then generates the spatial attention map 331. Then, the processor 110 may generate an output feature map 350 of the attention module by performing the element-wise multiplication 313 on the generated spatial attention map 331 and the modified feature map 330. The output feature map 350 of the attention module may have the form in which a value of a parameter for the main region is amplified and a value of a parameter irrelevant to the main region is offset when compared with the feature map 310 input to the attention module. The foregoing example is merely an example, and the present disclosure is not limited thereto.

The attention module in the embodiment of the present disclosure may include the channel attention neural network model for generating the channel attention map and the spatial attention neural network model for generating the spatial attention map as described above. The channel attention map may be generated for the feature map input to the attention module. The spatial attention map may be generated for the modified feature map. The modified feature map may be generated by multiplying, by the processor 110, the feature map input to the attention module by the channel attention map for each element. The processor 110 may generate an output feature map of the attention module by multiplying the modified feature map by the spatial attention map for each element. The output feature map of the attention module is the feature map in which the channel attention map and the spatial attention map are sequentially applied to the feature map input to the attention module, and has an effect of helping the bone age analysis model to intensively analyze the main region of the image.

In the embodiment of the present disclosure, the bone age analysis model may be trained through supervised learning based on an attention guide label. In the present disclosure, the attention guide label may mean data having an importance value for at least each pixel of a training image. The importance may be expressed with a discrete distribution or continuous distribution. For example, when the importance is expressed with the discrete distribution, the importance may be expressed with a binary discrete distribution including 0 and 1 or a multi-dimensional discrete distribution including two or more differential values. For another example, when the important is expressed with the continuous distribution, the importance may be expressed with a probability value within a predetermined (or selected) section. The probability value may include a normal distribution probability value.

In the embodiment of the present disclosure, in at least one pixel included in the training image, the attention guide label may include importance of the pixel obtained as a result of substituting a distance between the coordinates of the pixel and the coordinates of a center point of one or more main regions included in the training image to an equation based on Gaussian distribution. The importance of the pixel may exist for each pixel. The distance may include, for example, a Euclidean distance, a Manhattan distance, or a Chebyshev distance. As the embodiment, when the processor 110 calculates the importance of each pixel based on a Euclidean distance, an equation for the distance calculation may be expressed as Equation 1.

$$d(x,y,b_i)=\sqrt{(x-x_i)^2+(y-y_i)^2} \ (i \in \{1,2,\ldots,K\})  \quad \text{Equation 1}$$

In Equation 1, d( ) represents a distance function. (x, y) represents coordinates of the pixel included in the training image. $b_i$ is a symbol representing the $i^{th}$ main region when there are a total of k main regions, and $x_i$ and $y_i$ represents an x coordinate and a y coordinate of the center point of the $i^{th}$ main region in order. The processor 110 may calculate the importance of each pixel by substituting the distance value calculated according to Equation 1 to the equation based on the Gaussian distribution. The equation based on the Gaussian distribution may be expressed as Equation 2.

$$p(x,y)=\Sigma_{b_i \in B} \exp(-d(x,y,b_i)/\sigma(b_i)) \quad \text{Equation 2}$$

In Equation 2, p( ) represents a probability function. (x, y) represents coordinates of each pixel included in the training image. $b_i$ $b_i$ is a symbol representing the $i^{th}$ main region when there are a total of k main regions, and B represents a set of the entire main regions. The equation based on the Gaussian distribution expressed as Equation 2 has the importance of the pixel as a probability value. $\sigma(b_i)\sigma(b_i)$ represents the distribution for $b_i$ that is the $i^{th}$ main region. The $\sigma$ function representing the distribution may be expressed as Equation 3.

$$\sigma(b_i) = \max(w_i, h_i)/C \qquad \text{Equation 3}$$

$(w_i, h_i)(w_i, h_i)$ represents a width and a height when $b_i$ that is the $i^{th}$ main region is displayed as a rectangle. C represents a predetermined (or selected) value for the distribution calculation.

As described above, for one training image, when there are coordinates of the center point of at least one main region, the width of the main region, and the height of the main region, it is possible to calculate importance of the pixel for all of the pixels included in the training image by using Equations 1 to 3. The function related to the distance, the method for calculating the probability, and the like are merely the examples, and the present disclosure is not limited thereto.

Figure 4:
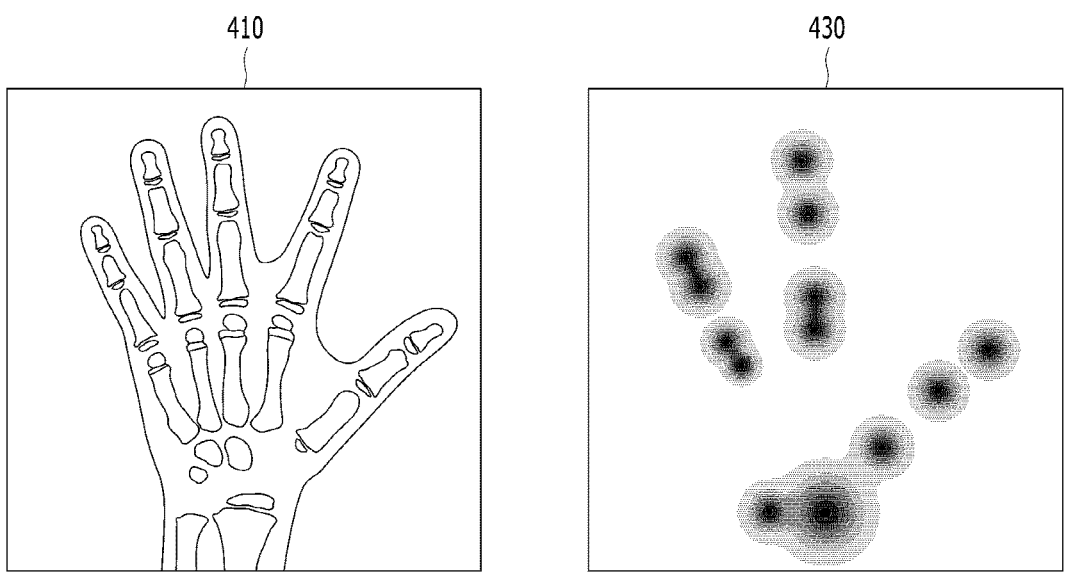
FIG. 4 is a diagram illustrating an example of a structure of an attention guide label according to the embodiment of the present disclosure.

FIG. 4 is a diagram illustrating an example of a structure of the attention guide label according to the embodiment of the present disclosure. When a major region in a carpal-related training image 410 is a region near at least one or more joint nodes, the processor 110 may calculate distances between all of the pixels included in the carpal-related training image 410 and the main region based on Equation 1. Then, the processor 110 may calculate the distribution for the main region based on Equation 3. A constant for the distribution calculation may also be set to 8. Then, the processor 110 may substitute the results of Equation 1 and Equation 3 to Equation 2 to finally calculate importance of all of the pixels included in the carpal-related training image 410. Reference numeral 430 of FIG. 4 is a diagram illustrating an example in which a pixel with higher importance is displayed in a darker color and a pixel with lower importance is displayed in a lighter color. The processor 110 may generate the attention guide label corresponding to the training image by the foregoing method.

In the embodiment of the present disclosure, the attention guide label may be generated based on a detection result obtained as a result of inputting, by the processor 110, the training image to the main region detection model including at least one neural network. The detection result may include location information about one or more main regions included in the training image. The training image may be the image for training the bone age analysis model of the present disclosure. The main region detection model may be the model which is formed of the CNN structure and detects one or more main regions from the input image and outputs the detected main region. At least one connection weight or bias included in the main region detection model may be learned through a separate training by the processor 110. At least one connection weight or bias included in the main region detection model may have been completely learned from the outside, transmitted through the network unit 150, and stored in the memory 130. As the embodiment, when the main region detection model is trained with the carpal-related training image, the main region detection model may detect an examination target region by the TW3 method from the carpal-related training image as the main region and output a detection result including location information about the main region. The detection result may be data including the location information about the main region included in the training image as a numerical value for each training image. As the embodiment, when the main region detected by the main region detection model is a quadrangular shape, the location information about the main region may include coordinates of four vertices. As another embodiment, when the main region detected by the main region detection model is a rectangular shape, the location information about the main region may include a middle point, a width, and a height of the rectangle. As another embodiment, when the main region detected by the main region detection model is a circular shape, the location information about the main region may include a middle point and a radius of the main region. The example of the location information is merely the example, and the present disclosure is not limited thereto.

In the embodiment of the present disclosure, when the main region is the form of a bounding box, the detection result using the main region detection model of the processor 110 may include coordinates of the center point of one or more main regions included in the training image, a width of the main region, and a height of the main region. The coordinates of the center point of the main region may be the middle point of the coordinates of the four vertices of the bounding box.

Figure 5:
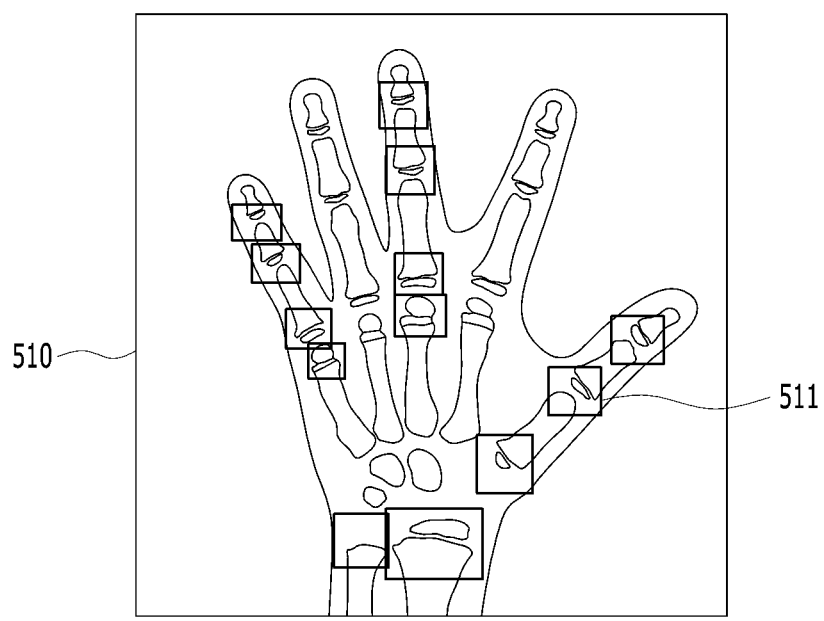
FIG. 5 is a diagram illustrating an example of a result using a main region detection model according to the embodiment of the present disclosure.

FIG. 5 is a diagram illustrating an example of a result using the main region detection model according to the embodiment of the present disclosure. The processor 110 may input a bone image 510 for the training of the main region detection model to the main region detection model, and then train the main region detection model so as to detect a main region 511 from the bone image 510. The training completed main region detection model may detect one or more main regions 511 for the input image, and include coordinates of the center point of the main region 511, a width of the main region 511, a height of the main region 511, and the like.

In the embodiment of the present disclosure, the attention guide label may also be generated based on a main region display result included in the training image of the user. The user may display one or more main regions for the training image, provide the processor 110 with the one or more displayed main regions as a main region display result, and generate an attention guide label corresponding to the training image. In particular, the user may display one or more main regions determined to be intensively analyzed by the bone age analysis model in the training image. The operation of displaying, by the user, the main region in the training image may include, for example, an operation of inputting at least one information among coordinates of a center point, a width of the main region, or a height of the main region when the main region is in the form of the bounding box. The processor 110 may recognize location information about the corresponding region from the main region display result of the user. For example, when the user displays the main region in the form of a rectangle, the processor 110 may recognize the coordinates of the center point, the width, and the height of the corresponding main region. The operation of displaying, by the user, the main region in the training image may be performed based on a separate image viewer program and the like. The processor 110 may generate an attention guide label through Equations 1 to 3 by using the training image and the main region display result of the user corresponding to the training image.

In another embodiment of the present disclosure, the user may directly generate the attention guide label for the training image. That is, the user may also directly perform the labelling operation of generating the attention guide label corresponding to the training image for the training image. For example, the user may directly input importance of one or more pixels included in the training image for the training to the processor 110. When the user performs the labelling operation on the training image, except for one or more pixels to which the user directly inputs importance of the pixel, the processor 110 may set the remaining pixels to have predetermined (or selected) importance. The predetermined (or selected) importance may be set to, for example, 0. The processor 110 may match the attention guide label labelled by the user and the training image corresponding to the attention guide label and utilize the matched training image for the training of the bone age analysis model.

Hereinafter, the supervised learning method of the bone age analysis model will be described. In the embodiment of the present disclosure, the bone age analysis model is trained through supervised learning based on one or more training images and an attention guide label which corresponds to each of the training images and includes one or more main regions, and the supervised learning may be performed based on a result of a comparison between a spatial attention map generated for the training image by using the bone age analysis model and the attention guide label corresponding to the training image. In the embodiment of the present disclosure, the bone age analysis model may use one or more loss values for the supervised learning of the model. One or more loss values may include regression loss according to the comparison between a bone age prediction value and actual age, or regression loss according to the comparison between the spatial attention map generated in the computation process by the bone age analysis model for the training image and the attention guide label. The processor 110 may update an internal connection weight or bias in a direction in which the loss value decreases during the training process of the one age analysis model. The processor 110 may use at least one of, for example, a root mean square error function, a mean square error function, a mean absolute value error function, a mean square log error function as the loss function for calculating the regression loss. Further, the processor 110 may also use a cross entropy function or a binary cross entropy function as the loss function for calculating the regression loss.

As described above, the processor 110 may compare the spatial attention map generated for the training image by the bone age analysis model for the supervised learning of the bone age analysis model and the attention guide label for the training image. The comparison includes the comparison of data corresponding to the elements at the same position in the array having the same size. When the size of the spatial attention map is smaller than the size of the attention guide label for the comparison, the processor 110 may perform upsampling on the spatial attention map. The upsampling may include unpooling. The upsampling may mean an operation of increasing height and width sizes of the spatial attention map in a spatial ratio. The data of the element of the array newly generated when the processor 110 increases the size of the spatial attention map in the specific ratio may be filled with 0 or a predetermined (or selected) number. The term "specific ratio" may be used interchangeably with the word "stride" and have the same meaning. For example, when the two-dimensional array having the size of 2×2 is upsampled by a stride of 32, the two-dimensional array has the size of 64×64. When the data of the elements of the newly generated array is filled with 0, the upsampled array having the size of 64×64 may include a total of 4 array elements having the data that is not 0. The foregoing example is merely an example, and the present disclosure is not limited thereto. In the present disclosure, even when the sizes of the spatial attention map and the attention guide label are different from each other by performing the upsampling like the foregoing example, the processor 110 may make the sizes of the two arrays be the same, compare the spatial attention map and the attention guide label, and then train the bone age analysis model based on the result of the comparison.

In the embodiment of the present disclosure, the supervised learning of the bone age analysis model performed by the processor 110 may be performed based on a result value calculated by substituting the spatial attention map and the attention guide label to a binary cross-entropy loss function. The spatial attention map may be used as a prediction value in the binary cross-entropy loss function. The attention guide label may be used as ground truth in the binary cross-entropy loss function. The binary cross-entropy loss function may be calculated and summed for each pixel of the spatial attention map. The binary cross-entropy loss function may be trained so that the result value is close to 0. An equation of the binary cross-entropy loss function is represented as Equation 4.

$$H_p(q) = -\frac{1}{N}\sum_{i=1}^{N}[y_i\log(p(y_i)) + (1-y_i)\log(1-p(y_i))] \quad \text{Equation 4}$$

In Equation 4, $y_i$ represents the label of the $i^{th}$ pixel included in the attention guide label. The label may be expressed as 0 or 1, when the importance of one or more pixels is larger than a predetermined (or selected) threshold value for the binary classification, the label may be determined as 1, or when the importance of one or more pixels is smaller than the predetermined (or selected) threshold value for the binary classification, the label may be determined as 0. The predetermined (or selected) threshold value for the binary classification may be arbitrarily set by the user. The predetermined (or selected) threshold value for the binary classification may also be set to a value corresponding to the upper M % in the normal distribution function after normalizing the entire distribution function of the importance values of one or more pixels. The M may be set by the user, such as 25 and 50. One or more pixels included in the spatial attention map in the two-dimensional array or the attention guide label may be ordered according to an arbitrary criterion. $p(y_i)$ of Equation 4 represents predicted importance of the $i^{th}$ pixel included in the spatial attention map generated by the processor 110 for the training image by using the attention module included in the bone age analysis model. The predicted importance may be normalized and set to have a value between 0 and 1. As another embodiment, the processor 110 may use a cross entropy function, not the binary cross entropy function, as the loss function. In the present disclosure, the processor 110 may train the attention model by updating the internal connection weights and biases of the channel attention neural network model and the spatial attention neural network model included in the attention model so that the loss value of the loss function is reduced or minimized.

In the embodiment of the present disclosure, when the bone age analysis model includes two or more attention modules, the supervised learning of the bone age analysis model may be performed based on a result obtained by multiplying the result value of the loss function calculated in each attention module by the weight of the predetermined (or selected) attention module and then summing the multiplication results. As an example for description, an equation is represented as Equation 5.

$$L = L_{reg} + \sum_{i} \lambda_i * L_{att_i} \qquad \text{Equation 5}$$

In Equation 5, L represents the entire loss values. $L_{reg}$ represents the loss value considering the difference between the bone age predicted by the bone age analysis model and the actual age. $L_{att_i}$ represents the loss value based on the result of the comparison between the spatial attention map and the attention guide label generated by the $i^{th}$ attention module. $\lambda_i$ represents the weight for the loss value of the $i^{th}$ attention module according to the attention module. As described above, in the present disclosure, when the processor 110 trains the bone age analysis model, the processor 110 progresses the training in consideration of the loss value based on the spatial attention map generated by one or more attention modules, as well as the regression loss value based on the predicted age according to the final output, thereby enabling the bone age analysis model to perform the analysis based on the main region of each part of the bone image. As a result, there is an effect of improving the overall bone age assessment performance. Further, in the present disclosure, when the bone age analysis model includes two or more attention modules, the processor 110 may determine the entire loss values by assigning the weight to the attention module. That is, the processor 110 may adjust the influence for each attention module in determining the entire loss value for the supervised learning. In the bone age analysis model of the present disclosure, when there are the plurality of attention modules, the attention module closer to an output end of the entire model is more likely to lose detailed location information of the input training image than the attention module located closer to an input end of the entire model during the computation process. In the above case, in the generation of the spatial attention map to intensively analyze the main region, the weight may be considered to give higher consideration of the loss of the attention module located at the side of the input end of the entire model which knows the detailed location information of the input training image more accurately. In the determination of the entire loss value by assigning the weight according to the attention module, the processor 110 adjusts the influence for each attention module, thereby obtaining the effective learning result.

In the embodiment of the present disclosure, the processor 110 of the computing device may provide a user interface screen including a heat map generated based on the spatial attention map for the analysis image generated by the attention module included in the bone age analysis model. After the training of the bone age analysis model is completed, the computing device 100 may receive the analysis image. The analysis image may be the new image that does not exist in the training image. In this case, for the analysis image, the attention guide label may not exist. The processor 110 may generate a heat map based on the spatial attention map for the analysis image. The processor 110 may provide the user with the user interface screen including the heat map. The heat map may be a visual representation of a spatial attention map generated by the attention module in the computation process for assessing, by the bone age analysis model, the bone age in the input analysis image. The visual representation of the heat map may be the representation based on color according to the size of the internal parameter value of the spatial attention map. For example, as the parameter value is larger, the heat map may be represented to be closer to red, and as the parameter value is smaller, the heat map may be represented to be closer to blue. The parameter may be the value calculated based on the importance of the corresponding pixel. The example of the representation of the heat map is merely illustrative, and the present disclosure is not limited thereto. The heat map may be included in a part of the user interface screen and provided to the user.

In the embodiment of the present disclosure, the computing device may further include an output unit (not illustrated). The output unit (not illustrated) may include at least one of a Liquid Crystal Display (LCD), a Thin Film Transistor Liquid Crystal Display (TFT LCD), an Organic Light Emitting Diode (OLED), a flexible display, and a 3D display. Among them, some display modules may be configured as a transparent type or a light transmission type so that the outside can be seen through the display modules. This may be referred to as a transparent display module, and a representative example of the transparent display module includes a Transparent OLED (TOLED). The computing device of the present disclosure provide the user interface screen including the heat map generated based on the spatial attention map for the analysis image generated by the processor 110 to the output unit (not illustrated) and display the user interface screen so that the user may see the user interface screen. Further, the computing device of the present disclosure may provide an external device with the user interface screen including the heat map generated based on the spatial attention map for the analysis image generated by the processor 110. The computing device of the present disclosure may transmit the user interface screen to the outside device through the network unit 150 and make the outside device to display the user interface screen to the user.

The bone age assessment method of the present disclosure provides the user with the user interface screen including the heat map generated based on the spatial attention map for the analysis image, so that there is an effect in that the user has improved reliability on a result inference of the analysis model and raises transparency of the model. Hereinafter, this will be illustratively described with reference to FIG. 6.

Figure 6:
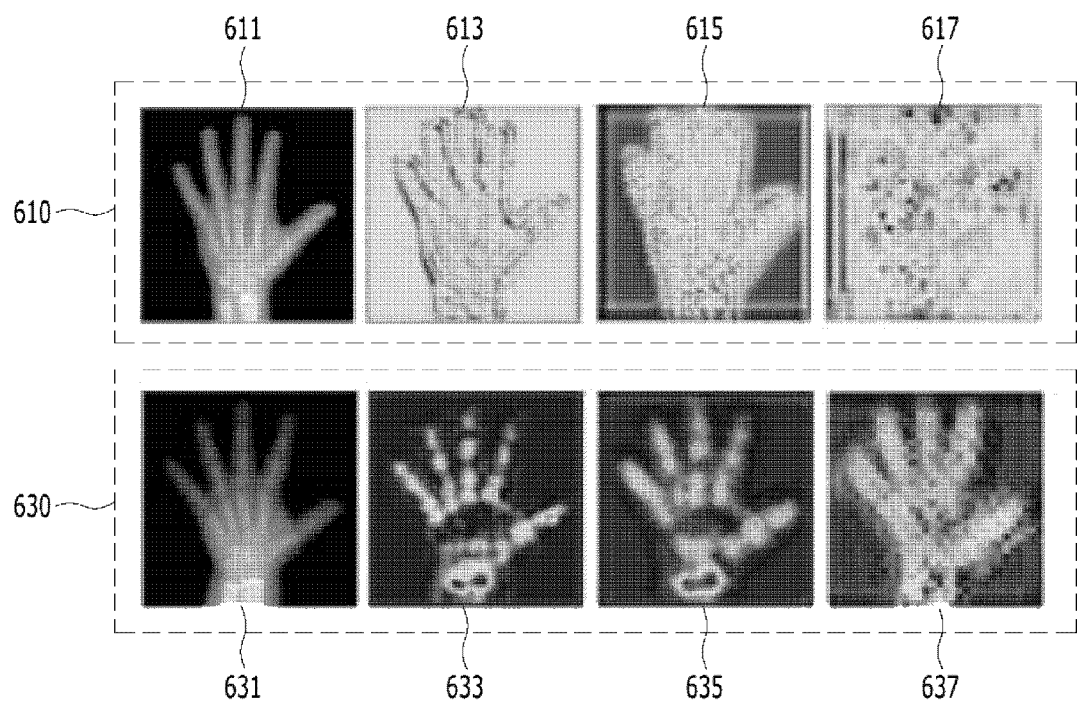
FIG. 6 is a diagram illustrating an example of a user interface screen including a heat map generated based on a spatial attention map for an analysis image according to the embodiment of the present disclosure.

FIG. 6 is a diagram illustrating an example of a user interface screen including a heat map generated based on a spatial attention map for an analysis image according to the embodiment of the present disclosure.

Reference numeral 630 of FIG. 6 includes a heat map that visually represents the spatial attention map generated in the bone age analysis model including the attention module that is trained with supervised learning. Investigating the region 630, when the bone age analysis model includes, for example, three attention modules, the bone age analysis model may generate the total of three spatial attention maps for a first carpal image 631 in the computation process. The heat maps visually representing the plurality of spatial attention maps may be represented as the color-based heat map according to importance. For example, the heat map visually representing the spatial attention map may be displayed by differently setting a color, brightness, concentration, and the like according to a difference in the importance value. As an example, for the pixel included in the heat map, as the importance is higher, the pixel may be displayed with red, and as the importance is lower, the pixel may be displayed with blue. For another example, for the pixel included in the heat map, as the importance is higher, the pixel may be displayed brighter, and as the importance is lower, the pixel may be displayed darker. The description of the representation method of the heat map is merely illustrative, and the present disclosure is not limited thereto. Referring to FIG. 6, it can be seen that as a first heat map 633, a second heat map 635, and a third heat map 637 for the plurality of spatial attention maps progress in the order, this is closer to the output end of the bone age analysis model, so that the degree of abstraction is high and thus resolution is decreased. Referring to the first heat map 633, the second heat map 635, and the third heat map 637, it can be seen that the bone age analysis model analyzes the knuckle or joint part, which is main region for assessing the bone age in the carpal image, with high importance. The processor 110 may provide the user interface screen including at least one of the first heat map 633, the second heat map 635, and the third heat map 637 to the user. In this case, the user may view the spatial attention map and check which part of the first carpal image 631 based on which the bone age analysis model assesses the bone age.

Reference numeral 610 of FIG. 6 includes a heat map visually representing a spatial attention map generated in the bone age analysis model including an attention module trained with non-supervised training. For example, the bone age analysis model trained with non-supervised training for the second carpal image 611 may generate three spatial attention maps, and the heat maps for the plurality of attention maps may be displayed with a fourth heat map 613, a fifth heat map 615, and a sixth heat map 617. This shows a contrasting result when compared with the first heat map 633, the second heat map 635, and the third heat map 637 derived by the bone age analysis model which is trained with the supervised learning of the present disclosure. In particular, in reference numeral 613, most of the pixels are expressed with green, which means that the first attention module which is trained with the non-supervised learning determines almost all areas of the carpal image as the main region and gives high importance to most of the pixels. That is, even though the bone age analysis model includes the attention module, but is not trained to intensively analyze the main region by the supervised learning using the attention guide label like the present disclosure, the bone age analysis model uses a computing resource in a region that do not need to be analyzed in assessing the bone age. Accordingly, the bone age analysis model including the attention module which is trained with the supervised learning according to the embodiment of the present disclosure has an advantage of effectively training the model and improving performance.

Figure 7:
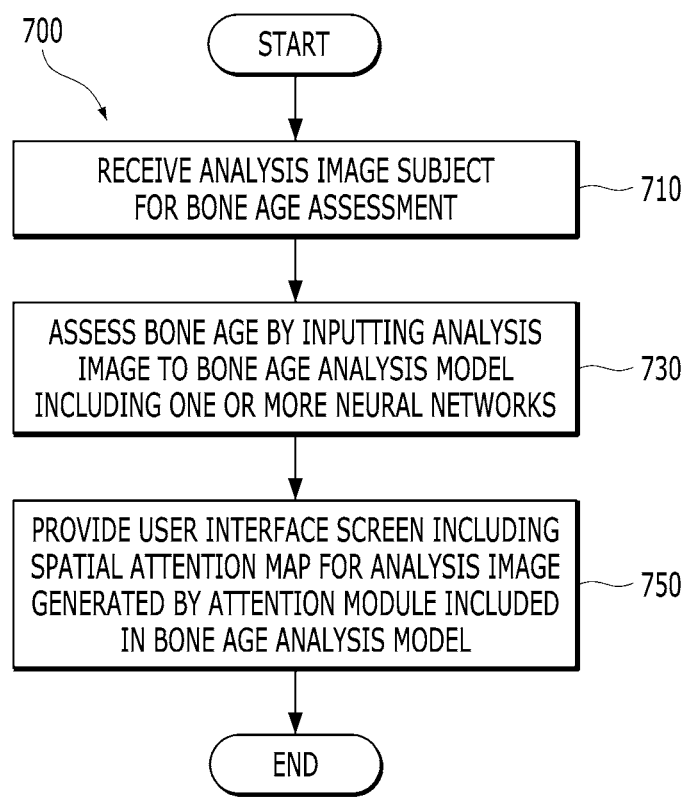
FIG. 7 is a flowchart for describing the case where the computing device assesses bone age for an analysis image and provides a user interface screen according to the embodiment of the present disclosure.

FIG. 7 is a flowchart for describing the case where the computing device assesses bone age for an analysis image and provides a user interface image according to the embodiment of the present disclosure. The network unit 150 of the computing device 100 of the present disclosure may receive an analysis image which is a target of bone age assessment (710). The analysis image may be an image different from an existing trained training image. The processor 110 of the computing device 100 may input the analysis image to a bone age analysis model including one or more neural networks and assess bone age (730). The bone age analysis model may include one or more attention modules for intensively analyzing a main region. The attention module may include a channel attention neural network model for generating a channel attention map and a spatial attention neural network model for generating a spatial attention map. Then, the processor 110 of the computing device 100 may provide a user interface screen including a heat map generated based on the spatial attention map for the analysis image generated by the attention module included in the bone age analysis model (750). By checking the spatial attention map for the analysis image, the user may easily recognize the part from which the bone age analysis model derives the conclusion.

Figure 8:
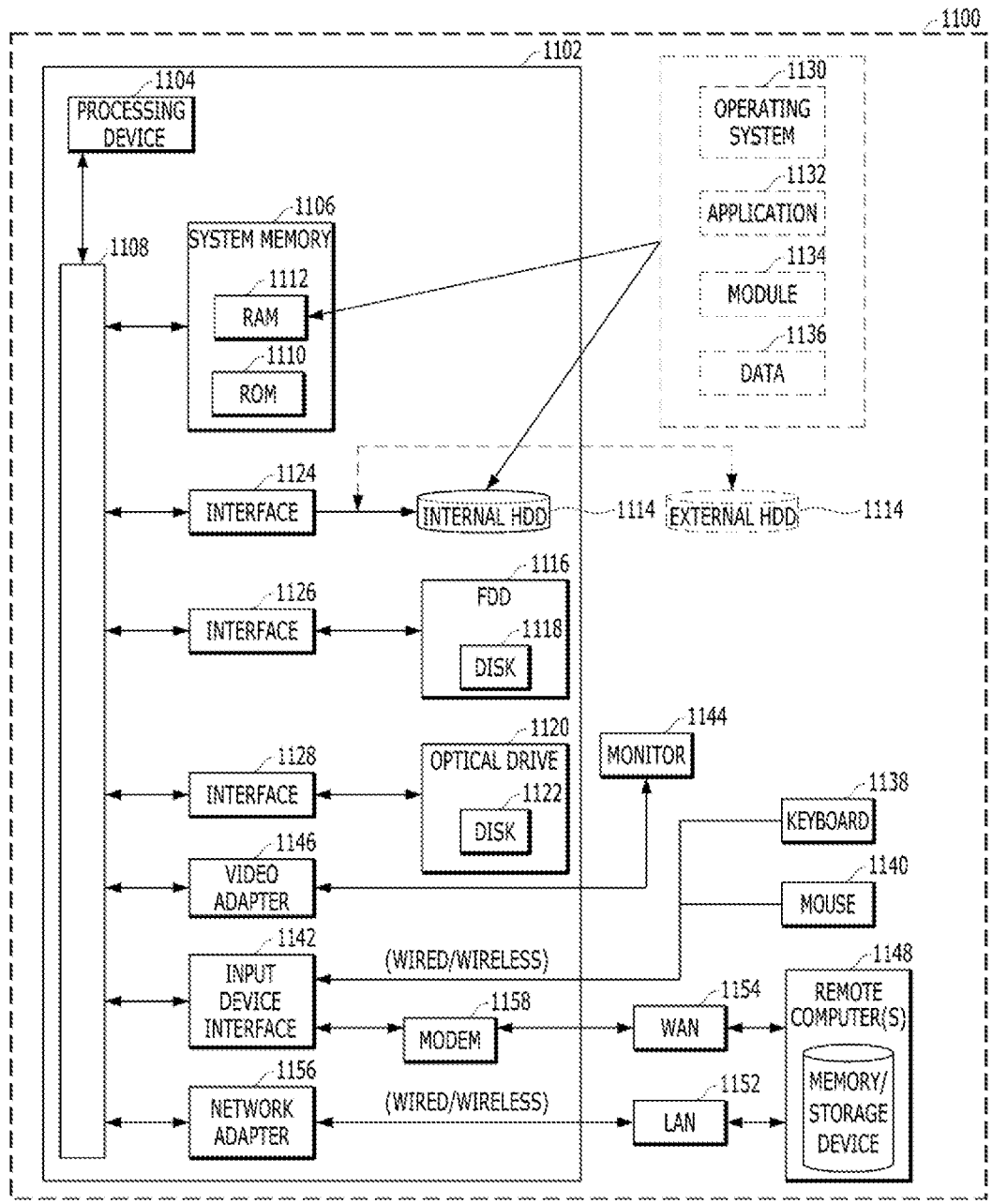
FIG. 8 is a simple and general schematic diagram for an example of a computing environment in which the embodiments of the present disclosure are implementable.

FIG. 8 is a simple and normal schematic view of a computing environment in which the embodiments of the present disclosure may be implemented.

It is described above that the present disclosure may be generally implemented by the computing device, but those skilled in the art will well know that the present disclosure may be implemented in association with a computer executable command which may be executed on one or more computers and/or in combination with other program modules and/or as a combination of hardware and software.

In general, the program module includes a routine, a program, a component, a data structure, and the like that execute a specific task or implement a specific abstract data type. Further, it will be well appreciated by those skilled in the art that the method of the present disclosure can be implemented by other computer system configurations including a personal computer, a handheld computing device, microprocessor-based or programmable home appliances, and others (the respective devices may operate in connection with one or more associated devices as well as a single-processor or multi-processor computer system, a mini computer, and a main frame computer.

The embodiments described in the present disclosure may also be implemented in a distributed computing environment in which predetermined (or selected) tasks are performed by remote processing devices connected through a communication network. In the distributed computing environment, the program module may be positioned in both local and remote memory storage devices.

The computer generally includes various computer readable media. Media accessible by the computer may be computer readable media regardless of types thereof and the computer readable media include volatile and non-volatile media, transitory and non-transitory media, and mobile and non-mobile media. As a non-limiting example, the computer readable media may include both computer readable storage media and computer readable transmission media. The computer readable storage media include volatile and non-volatile media, temporary and non-temporary media, and movable and non-movable media implemented by a predetermined (or selected) method or technology for storing information such as a computer readable instruction, a data structure, a program module, or other data. The computer readable storage media include a RAM, a ROM, an EEPROM, a flash memory or other memory technologies, a CD-ROM, a digital video disk (DVD) or other optical disk storage devices, a magnetic cassette, a magnetic tape, a magnetic disk storage device or other magnetic storage devices or predetermined (or selected) other media which may be accessed by the computer or may be used to store desired (or selected) information, but are not limited thereto.

The computer readable transmission media generally implement the computer readable command, the data structure, the program module, or other data in a carrier wave or a modulated data signal such as other transport mechanism and include all information transfer media. The term "modulated data signal" means a signal acquired by configuring or changing at least one of characteristics of the signal so as to encode information in the signal. As a non-limiting example, the computer readable transmission media include wired media such as a wired network or a direct-wired connection and wireless media such as acoustic, RF, infrared and other wireless media. A combination of any media among the aforementioned media is also included in a range of the computer readable transmission media.

An environment 1100 that implements various aspects of the present disclosure including a computer 1102 is shown and the computer 1102 includes a processing device 1104, a system memory 1106, and a system bus 1108. The system bus 1108 connects system components including the system memory 1106 (not limited thereto) to the processing device 1104. The processing device 1104 may be a predetermined (or selected) processor among various commercial processors. A dual processor and other multi-processor architectures may also be used as the processing device 1104.

The system bus 1108 may be any one of several types of bus structures which may be additionally interconnected to a local bus using any one of a memory bus, a peripheral device bus, and various commercial bus architectures. The system memory 1106 includes a read only memory (ROM) 1110 and a random access memory (RAM) 1112. A basic input/output system (BIOS) is stored in the non-volatile memories 1110 including the ROM, the EPROM, the EEPROM, and the like and the BIOS includes a basic routine that assists in transmitting information among components in the computer 1102 at a time such as in-starting. The RAM 1112 may also include a high-speed RAM including a static RAM for caching data, and the like.

The computer 1102 also includes an interior hard disk drive (HDD) 1114 (for example, EIDE and SATA), in which the interior hard disk drive 1114 may also be configured for an exterior purpose in an appropriate chassis (not illustrated), a magnetic floppy disk drive (FDD) 1116 (for example, for reading from or writing in a mobile diskette 1118), and an optical disk drive 1120 (for example, for reading a CD-ROM disk 1122 or reading from or writing in other high-capacity optical media such as the DVD, and the like). The hard disk drive 1114, the magnetic disk drive 1116, and the optical disk drive 1120 may be connected to the system bus 1108 by a hard disk drive interface 1124, a magnetic disk drive interface 1126, and an optical drive interface 1128, respectively. An interface 1124 for implementing an exterior drive includes at least one of a universal serial bus (USB) and an IEEE 1394 interface technology or both of them.

The drives and the computer readable media associated therewith provide non-volatile storage of the data, the data structure, the computer executable instruction, and others. In the case of the computer 1102, the drives and the media correspond to storing of predetermined (or selected) data in an appropriate digital format. In the description of the computer readable media, the mobile optical media such as the HDD, the mobile magnetic disk, and the CD or the DVD are mentioned, but it will be well appreciated by those skilled in the art that other types of media readable by the computer such as a zip drive, a magnetic cassette, a flash memory card, a cartridge, and others may also be used in an operating environment and further, the predetermined (or selected) media may include computer executable commands for executing the methods of the present disclosure.

Multiple program modules including an operating system 1130, one or more application programs 1132, other program module 1134, and program data 1136 may be stored in the drive and the RAM 1112. All or some of the operating system, the application, the module, and/or the data may also be cached in the RAM 1112. It will be well appreciated that the present disclosure may be implemented in operating systems which are commercially usable or a combination of the operating systems.

A user may input instructions and information in the computer 1102 through one or more wired/wireless input devices, for example, pointing devices such as a keyboard 1138 and a mouse 1140. Other input devices (not illustrated) may include a microphone, an IR remote controller, a joystick, a game pad, a stylus pen, a touch screen, and others. These and other input devices are often connected to the processing device 1104 through an input device interface 1142 connected to the system bus 1108, but may be connected by other interfaces including a parallel port, an IEEE 1394 serial port, a game port, a USB port, an IR interface, and others.

A monitor 1144 or other types of display devices are also connected to the system bus 1108 through interfaces such as a video adapter 1146, and the like. In addition to the monitor 1144, the computer generally includes other peripheral output devices (not illustrated) such as a speaker, a printer, others.

The computer 1102 may operate in a networked environment by using a logical connection to one or more remote computers including remote computer(s) 1148 through wired and/or wireless communication. The remote computer(s) 1148 may be a workstation, a computing device computer, a router, a personal computer, a portable computer, a micro-processor based entertainment apparatus, a peer device, or other general network nodes and generally includes multiple components or all of the components described with respect to the computer 1102, but only a memory storage device 1150 is illustrated for brief description. The illustrated logical connection includes a wired/wireless connection to a local area network (LAN) 1152 and/or a larger network, for example, a wide area network (WAN) 1154. The LAN and WAN networking environments are general environments in offices and companies and facilitate an enterprise-wide computer network such as Intranet, and all of them may be connected to a worldwide computer network, for example, the Internet.

When the computer 1102 is used in the LAN networking environment, the computer 1102 is connected to a local network 1152 through a wired and/or wireless communication network interface or an adapter 1156. The adapter 1156 may facilitate the wired or wireless communication to the LAN 1152 and the LAN 1152 also includes a wireless access point installed therein in order to communicate with the wireless adapter 1156. When the computer 1102 is used in the WAN networking environment, the computer 1102 may include a modem 1158 or has other means that configure communication through the WAN 1154 such as connection to a communication computing device on the WAN 1154 or connection through the Internet. The modem 1158 which may be an internal or external and wired or wireless device is connected to the system bus 1108 through the serial port interface 1142. In the networked environment, the program modules described with respect to the computer 1102 or some thereof may be stored in the remote memory/storage device 1150. It will be well known that an illustrated network connection is and other means configuring a communication link among computers may be used.

The computer 1102 performs an operation of communicating with predetermined (or selected) wireless devices or entities which are disposed and operated by the wireless communication, for example, the printer, a scanner, a desktop and/or a portable computer, a portable data assistant (PDA), a communication satellite, predetermined (or selected) equipment or place associated with a wireless detectable tag, and a telephone. This at least includes wireless fidelity (Wi-Fi) and Bluetooth wireless technology. Accordingly, communication may be a predefined structure like the network in the related art or just ad hoc communication between at least two devices.

The wireless fidelity (Wi-Fi) enables connection to the Internet, and the like without a wired cable. The Wi-Fi is a wireless technology such as the device, for example, a cellular phone which enables the computer to transmit and receive data indoors or outdoors, that is, anywhere in a communication range of a base station. The Wi-Fi network uses a wireless technology called IEEE 802.11(a, b, g, and others) in order to provide safe, reliable, and high-speed wireless connection. The Wi-Fi may be used to connect the computers to each other or the Internet and the wired network (using IEEE 802.3 or Ethernet). The Wi-Fi network may operate, for example, at a data rate of 11 Mbps (802.11a) or 54 Mbps (802.11b) in unlicensed 2.4 and 5 GHz wireless bands or operate in a product including both bands (dual bands).

It will be appreciated by those skilled in the art that information and signals may be expressed by using various different predetermined (or selected) technologies and techniques. For example, data, instructions, commands, information, signals, bits, symbols, and chips which may be referred in the above description may be expressed by voltages, currents, electromagnetic waves, magnetic fields or particles, optical fields or particles, or predetermined (or selected) combinations thereof.

It may be appreciated by those skilled in the art that various logical blocks, modules, processors, means, circuits, and algorithm steps described in association with the embodiments disclosed herein may be implemented by electronic hardware, various types of programs or design codes (for easy description, herein, designated as software), or a combination of all of them. In order to clearly describe the intercompatibility of the hardware and the software, various components, blocks, modules, circuits, and steps have been generally described above in association with functions thereof. Whether the functions are implemented as the hardware or software depends on design restrictions given to a specific application and an entire system. Those skilled in the art of the present disclosure may implement functions described by various methods with respect to each specific application, but it should not be interpreted that the implementation determination departs from the scope of the present disclosure.

Various embodiments presented herein may be implemented as manufactured articles using a method, an apparatus, or a standard programming and/or engineering technique. The term manufactured article includes a computer program, a carrier, or a medium which is accessible by a predetermined (or selected) computer-readable storage device. For example, a computer-readable storage medium includes a magnetic storage device (for example, a hard disk, a floppy disk, a magnetic strip, or the like), an optical disk (for example, a CD, a DVD, or the like), a smart card, and a flash memory device (for example, an EEPROM, a card, a stick, a key drive, or the like), but is not limited thereto. Further, various storage media presented herein include one or more devices and/or other machine-readable media for storing information.

It will be appreciated that a specific order or a hierarchical structure of steps in the presented processes is one example of accesses. It will be appreciated that the specific order or the hierarchical structure of the steps in the processes within the scope of the present disclosure may be rearranged based on design priorities. Appended method claims provide elements of various steps in a sample order, but the method claims are not limited to the presented specific order or hierarchical structure.

The description of the presented embodiments is provided so that those skilled in the art of the present disclosure use or implement the present disclosure. Various modifications of the embodiments will be apparent to those skilled in the art and general principles defined herein can be applied to other embodiments without departing from the scope of the present disclosure. Therefore, the present disclosure is not limited to the embodiments presented herein, but should be interpreted within the widest range which is coherent with the principles and new features presented herein.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for bone age assessment using a neural network performed by a computing device, the method comprising:
   receiving an analysis image which is a target of bone age assessment; and
   assessing bone age of the target by inputting the analysis image into a bone age analysis model comprising one or more neural networks,
   wherein the bone age analysis model, which is trained by supervised learning based on an attention guide label, comprises at least one attention module for analyzing a main region of the analysis image,
   wherein the attention guide label comprises importance of each pixel obtained based on a distance between the each pixel included in a training image for training the bone age analysis model and the main region,
   wherein the supervised learning is performed based on a comparison result of a spatial attention map generated regarding the training image using the bone age analysis model and the attention guide label corresponding to the training image,
   wherein the supervised learning is performed based on:
      calculating a loss function by using a label of each pixel included in the attention guide label as a ground truth value and using predicted importance of each pixel included in the spatial attention map as a prediction value, and
      updating weights of the attention module so the loss function is minimized.

2. The method of claim 1, wherein the attention guide label is generated based on a detection result obtained as a result of inputting the training image to a main region detection model comprising at least one neural network, and
   wherein the detection result comprises location information on at least one main region comprised in the training image.

3. The method of claim 2, wherein when the main region is in a form of a bounding box, the detection result comprises coordinates of a center point of at least one main region comprised in the training image, a width of the at least one main region comprised in the training image, and a height of the at least one main region comprised in the training image.

4. The method of claim 1, wherein the attention guide label comprises an importance of at least one pixel comprised in the training image, and
wherein the pixel is obtained as a result of substituting a distance between coordinates of the pixel and coordinates of a center point of one or more main regions comprised in the training image to an equation based on a gaussian distribution.

5. The method of claim 1, wherein the bone age analysis model is trained by supervised learning based on at least one training image and the attention guide label which corresponds to each training image and comprises at least one main region.

6. The method of claim 5, wherein the supervised learning is performed based on a result calculated by substituting the spatial attention map and the attention guide label into a binary cross-entropy loss function.

7. The method of claim 1, wherein when the bone age analysis model comprises at least two attention modules, the supervised learning on the bone age analysis model is performed based on a result of multiplying a result of a loss function calculated in each attention module by the weight for a loss value of an attention module according to a predetermined attention module and then summing the multiplication results.

8. The method of claim 1, wherein the attention module comprises a channel attention neural network model for generating a channel attention map regarding a feature map input to the attention module, and a spatial attention neural network model for generating a spatial attention map regarding a modified feature map, and
wherein the modified feature map is a feature map generated by multiplying the feature map input to the attention module by the channel attention map for each element.

9. A method for bone age assessment using a neural network performed by a computing device, the method comprising:
receiving an analysis image which is a target of bone age assessment;
assessing bone age of the target by inputting the analysis image into a bone age analysis model comprising at least one neural network; and
providing a user interface screen comprising a heat map generated based on a spatial attention map for the analysis image,
wherein the bone age analysis model, which is trained by supervised learning based on an attention guide label, comprises at least one attention module for analyzing a main region of the analysis image,
wherein attention guide label comprises importance of each pixel obtained based on a distance between the each pixel included in a training image for training the bone age analysis model and the main region,
wherein the supervised learning is performed based on a comparison result of a spatial attention map generated regarding the training image using the bone age analysis model and the attention guide label corresponding to the training image,
wherein the supervised learning is performed based on:
calculating a loss function by using a label of each pixel included in the attention guide label as a ground truth value and using predicted importance of each pixel included in the spatial attention map as a prediction value, and
updating weights of the attention module so the loss function is minimized.

10. A computing device for bone age assessment, comprising:
one or more processors;
a memory for storing a bone age analysis model comprising one or more neural networks; and
a network unit for receiving an analysis image which is a target of bone age assessment,
and wherein the one or more processors is configured to:
assess bone age of the target by inputting the analysis image into a bone age analysis model comprising one or more neural networks,
wherein the bone age analysis model, which is trained by supervised learning based on an attention guide label, comprises at least one attention module for analyzing a main region of the analysis image,
wherein attention guide label comprises importance of each pixel obtained based on a distance between the each pixel included in a training image for training the bone age analysis model and the main region,
wherein the supervised learning is performed based on a comparison result of a spatial attention map generated regarding the training image using the bone age analysis model and the attention guide label corresponding to the training image,
wherein the supervised learning is performed based on:
calculating a loss function by using a label of each pixel included in the attention guide label as a ground truth value and using predicted importance of each pixel included in the spatial attention map as a prediction value, and
updating weights of the attention module so the loss function is minimized.

* * * * *